United States Patent
Anderberg et al.

(10) Patent No.: US 10,408,828 B2
(45) Date of Patent: Sep. 10, 2019

(54) LATERAL FLOW ASSAY WITH TEST STRIP RETAINER

(71) Applicant: ASTUTE MEDICAL, INC., San Diego, CA (US)

(72) Inventors: Joseph Anderberg, Encinitas, CA (US); John Van Bosch, Ventura, CA (US)

(73) Assignee: Astute Medical, Inc., San Diego, CA (US)

( * ) Notice: Subject to any disclaimer, the term of this patent is extended or adjusted under 35 U.S.C. 154(b) by 336 days.

(21) Appl. No.: 14/770,451

(22) PCT Filed: Feb. 25, 2014

(86) PCT No.: PCT/US2014/018303
§ 371 (c)(1),
(2) Date: Aug. 25, 2015

(87) PCT Pub. No.: WO2014/134033
PCT Pub. Date: Sep. 4, 2014

(65) Prior Publication Data
US 2016/0011188 A1    Jan. 14, 2016

Related U.S. Application Data

(60) Provisional application No. 61/769,709, filed on Feb. 26, 2013.

(51) Int. Cl.
*G01N 33/543* (2006.01)
*G01N 33/52* (2006.01)
(Continued)

(52) U.S. Cl.
CPC ...... *G01N 33/54386* (2013.01); *B01L 3/5023* (2013.01); *B01L 3/502707* (2013.01);
(Continued)

(58) Field of Classification Search
CPC .......... G01N 33/54386; G01N 33/558; G01N 33/525; B01L 3/502707; B01L 3/5023;
(Continued)

(56) References Cited

U.S. PATENT DOCUMENTS 4,477,575 A * 10/1984 Vogel ................ B01D 39/2017
                                                    210/509
4,689,202 A    8/1987 Khoja et al.
(Continued)

FOREIGN PATENT DOCUMENTS

| WO | 1992001226 A1 | 1/1992 |
| WO | 1998022824 A1 | 5/1998 |
| WO | 2007063423 A1 | 6/2007 |

OTHER PUBLICATIONS

International Search Report and Written Opinion dated May 21, 2014 in PCT/US2014/018303 (12 pages).
(Continued)

*Primary Examiner* — Dennis White
(74) *Attorney, Agent, or Firm* — Womble Bond Dickinson (US) LLP

(57) ABSTRACT

It is an object of the present invention to provide improved methods and compositions for manufacture and use of lateral flow test devices. In particular, the present invention provides a molding method which provides one or more features in the housing base configured to retain the test strip within the base. These features are provided as undercuts in the housing base. The test strip is configured as a bibulous lateral flow material disposed on a substantially non-compressible base layer, and the base layer is positioned within the undercut in order to retain the test strip in the housing base. Optionally, one or more features in the housing base which create the undercut are configured to engage the bibulous lateral flow material by compression and/or fric-
(Continued)

tion, thereby increasing the ability of the base to maintaining the test strip in its proper position within the device.

9 Claims, 4 Drawing Sheets

(51) Int. Cl.
*G01N 33/558* (2006.01)
*B01L 3/00* (2006.01)
*B29C 45/44* (2006.01)

(52) U.S. Cl.
CPC .......... *B29C 45/44* (2013.01); *B29C 45/4407* (2013.01); *G01N 33/525* (2013.01); *G01N 33/558* (2013.01); *B01L 2200/12* (2013.01); *B01L 2300/043* (2013.01); *B01L 2300/0609* (2013.01); *B01L 2300/069* (2013.01); *B01L 2300/0825* (2013.01); *B01L 2300/0887* (2013.01); *B29C 2045/4492* (2013.01)

(58) Field of Classification Search
CPC ....... B01L 2300/069; B01L 2300/0825; B01L 2300/0887; B01L 2200/12; B01L 2300/043; B01L 2300/0609; B29C 45/44; B29C 45/4407; B29C 2045/4492
See application file for complete search history.

(56) References Cited

U.S. PATENT DOCUMENTS

| | | | |
|---|---|---|---|
| 4,703,017 A | 10/1987 | Campbell et al. | |
| 4,743,560 A | 5/1988 | Campbell et al. | |
| 4,783,056 A | 11/1988 | Abrams | |
| 4,942,522 A | 7/1990 | Wilkie et al. | |
| 4,956,302 A | 9/1990 | Gordon et al. | |
| 5,073,484 A | 12/1991 | Swanson et al. | |
| 5,120,643 A | 6/1992 | Ching et al. | |
| 5,252,496 A | 10/1993 | Kang et al. | |
| 5,559,041 A | 9/1996 | Kang et al. | |
| 5,591,645 A | 1/1997 | Rosenstein | |
| 5,597,532 A | 1/1997 | Connolly | |
| 5,602,040 A | 2/1997 | May et al. | |
| 5,622,871 A | 4/1997 | May et al. | |
| 5,654,162 A | 8/1997 | Guire et al. | |
| 5,656,448 A | 8/1997 | Kang et al. | |
| 5,656,503 A | 8/1997 | May et al. | |
| 5,714,389 A | 2/1998 | Charlton et al. | |
| 5,728,587 A | 3/1998 | Kang et al. | |
| 5,989,921 A | 11/1999 | Charlton et al. | |
| 6,020,147 A | 2/2000 | Guire et al. | |
| 6,027,943 A | 2/2000 | Kang et al. | |
| 6,150,178 A | 11/2000 | Cesarczyk et al. | |
| 6,187,598 B1 | 2/2001 | May et al. | |
| 6,228,660 B1 | 5/2001 | May et al. | |
| 6,352,862 B1 | 3/2002 | Davis et al. | |
| 6,485,982 B1 | 11/2002 | Charlton | |
| 6,506,612 B2 | 1/2003 | Kang et al. | |
| 6,534,320 B2 | 3/2003 | Ching et al. | |
| 6,541,277 B1 | 4/2003 | Kang et al. | |
| RE38,430 E | 2/2004 | Rosenstein | |
| 6,737,277 B1 | 5/2004 | Kang et al. | |
| 6,818,455 B2 | 11/2004 | May et al. | |
| 2001/0008774 A1 | 7/2001 | May et al. | |
| 2003/0143755 A1 | 7/2003 | Davis et al. | |
| 2003/0207465 A1 | 11/2003 | Davis et al. | |
| 2003/0219908 A1 | 11/2003 | Davis et al. | |
| 2004/0082878 A1 | 4/2004 | Bldwin et al. | |
| 2005/0244986 A1 | 11/2005 | May et al. | |
| 2006/0040405 A1 | 2/2006 | Charlton et al. | |
| 2008/0112848 A1* | 5/2008 | Huffstodt | G01N 21/78 422/68.1 |
| 2010/0239460 A1 | 9/2010 | Nazareth et al. | |

OTHER PUBLICATIONS

Office Action issued by SIPO in Chinese patent application No. 2014800176011 dated May 26, 2016—incl Engl lang transl.
Extended European Search Report issued in EP 14757350 dated Aug. 16, 2016.
Mark et al., Microfluidic lab-on-a-chip platforms: requirements, characteristics and applications. Chem Sac Rev. Mar. 2010;39(3):1153-1182.

* cited by examiner

LATERAL FLOW ASSAY WITH TEST STRIP RETAINER

The present invention is filed under 35 U.S.C. § 371 as the U.S. national phase of International Application No. PCT/US2014/018303, filed Feb. 25, 2014, which designated the U.S. and claims the benefit of U.S. Provisional Application No. 61/769,709, filed Feb. 26, 2013, which is hereby incorporated by reference in its entirety including all tables, figures, and claims.

BACKGROUND OF THE INVENTION

The following discussion of the background of the invention is merely provided to aid the reader in understanding the invention and is not admitted to describe or constitute prior art to the present invention.

Lateral flow assay devices are widely used in many different areas of analytical chemistry and medicine, and have become the format of choice for tests such as immunoassays which are to be performed by relatively untrained users in a rapid testing protocol. Typically, the devices and methods allow for application of a sample to a lateral flow matrix. The sample flows along the lateral flow matrix, and one or more analyte components to be detected in the sample react with at least one reagent which is provided in or added to the lateral flow matrix. At least one reagent is typically immobilized in the device for reaction with the analyte component to be detected or a reagent thereof, and labels are typically employed to measure the extent of reaction with an immobilized reagent. See, e.g., U.S. patents and patent application publications: U.S. Pat. Nos. 5,602,040; 5,622,871; 5,656,503; 6,187,598; 6,228,660; 6,818,455; 2001/0008774; 2005/0244986; U.S. Pat. No. 6,352,862; 2003/0207465; 2003/0143755; 2003/0219908; U.S. Pat. Nos. 5,714,389; 5,989,921; 6,485,982; Ser. No. 11/035,047; U.S. Pat. Nos. 5,656,448; 5,559,041; 5,252,496; 5,728,587; 6,027,943; 6,506,612; 6,541,277; 6,737,277 B1; 5,073,484; 5,654,162; 6,020,147; 4,956,302; 5,120,643; 6,534,320; 4,942,522; 4,703,017; 4,743,560; 5,591,645; and RE 38,430.

Lateral flow assay devices may comprise a housing having a sample port and a result window downstream of the sample port, and, optionally, a control window downstream of the result window. The sample port is adapted to receive a quantity of liquid buffer or sample applied thereto which traverses a lateral flow path via a lateral flow matrix within the housing, extending from the sample port to a downstream location. The housing may be formed of any suitable material, an example of which comprises molded plastic, and is preferably sufficiently rigid to provide support and stability for the lateral flow path or paths housed therein adhesive may be is assembled on a housing surface with the adhesive facing the lateral flow matrix to assist in maintaining the lateral flow matrix in position within the housing.

WO2007/063423 discloses a lateral flow device in which the housing also comprises one or more pressure bars, supports and/or locating pegs for arranging the various layers and strips in the housing and maintaining them in position in the assembled device. For example, the housing top may be provided with a pressure bar for maintaining the upstream portion of the lower wicks in place at the buffer well and a pressure bar for maintaining the downstream ends of the lower wicks and the upstream ends of the main strips in contact with one another and in place in the assembled device. In one embodiment, these pressure bars may be formed integrally with the housing top, for example when the housing top is formed of molded plastic. Alternatively, one or more of the pressure bars may be provided as separate components.

SUMMARY OF THE INVENTION

It is an object of the present invention to provide improved methods and compositions for manufacture and use of lateral flow test devices. In particular, the present invention provides a molding method which provides one or more features in the housing base configured to retain the test strip within the base. These features are provided as undercuts (a design feature that obstructs the smooth opening of the mold or part ejection from the mold (without distorting or destroying the nominal design part geometry) in the housing base. The test strip is configured as a bibulous lateral flow material disposed on a substantially non-compressible base layer, and the base layer is positioned within the undercut in order to retain the test strip in the housing base. Optionally, one or more features in the housing base which create the undercut are configured to engage the bibulous lateral flow material by compression and/or friction, thereby increasing the ability of the base to maintaining the test strip in its proper position within the device.

Thus, in a first aspect, the present invention provides methods for forming a lateral flow test device. These methods comprise:

providing a first mold assembly which forms a test device base, the test device base comprising on a floor thereof a first vertical wall and a second vertical wall forming a recess having a defined width there between, the first vertical wall comprising one or more first structures and the second vertical wall comprising one or more second structures, wherein the first and second structures define an undercut portion between the first vertical wall and second vertical wall;

introducing a moldable material into the first mold assembly to form the test device base;

removing the test device base from the first mold assembly;

providing a test strip comprising
  a substantially uncompressible base layer,
  a first bibulous material disposed on the base layer at a proximal end thereof and forming a sample receiving region,
  a second bibulous material disposed on the base layer at a distal end thereof and forming an absorbent region, wherein the second bibulous material is compressible, and
  a porous membrane disposed on the base layer between the proximal and distal ends thereof and fluidly connected to the first bibulous material and the second bibulous material,
  the test strip defining a flow path wherein a sample applied to the sample receiving region flows through the porous membrane to the absorbent region, wherein the porous membrane comprises one or more test zones, each test zone comprising one or more reagents configured to bind for detection one or more analyte of interest; and inserting the test strip into the test device base such that the base layer inserts into the undercut portion, where the second bibulous material is optionally compressibly and/or frictionally engaged by the first structures and the second structures.

In a related aspect, the present invention provides methods of assembling a lateral flow test device. These methods comprise:

providing a test strip comprising
- a substantially uncompressible base layer,
- a first bibulous material disposed on the base layer at a proximal end thereof and forming a sample receiving region,
- a second bibulous material disposed on the base layer at a distal end thereof and forming an absorbent region, wherein the second bibulous material is compressible, and
- a porous membrane disposed on the base layer between the proximal and distal ends thereof and fluidly connected to the first bibulous material and the second bibulous material,
- the test strip defining a flow path wherein a sample applied to the sample receiving region flows through the porous membrane to the absorbent region, wherein the porous membrane comprises one or more test zones, each test zone comprising one or more reagents configured to bind for detection one or more analyte of interest;

providing a generally rigid base which supports the test strip, the base comprising a first vertical wall and a second vertical wall forming a recess which receives the base layer therewithin at the distal end of the base layer, the width of the recess being approximately equal to the width dimension of the base layer, the first vertical wall comprising one or more first structures formed thereon above the level of the base layer, and the second vertical wall comprising one or more second structures formed thereon above the level of the base layer, wherein the first and second structures are configured to retain the test strip within the base; and inserting the test strip into the test device base such that the base layer inserts into the undercut portion, where the second bibulous material is optionally engaged by the first compression structures and the second compression structures.

In another related aspect, the present invention provides lateral flow analyte test devices, comprising:

(a) a test strip comprising
- a substantially uncompressible base layer,
- a first bibulous material disposed on the base layer at a proximal end thereof and forming a sample receiving region,
- a second bibulous material disposed on the base layer at a distal end thereof and forming an absorbent region, wherein the second bibulous material is compressible, and
- a porous membrane disposed on the base layer between the proximal and distal ends thereof and fluidly connected to the first bibulous material and the second bibulous material,
- the test strip defining a flow path wherein a sample applied to the sample receiving region flows through the porous membrane to the absorbent region, wherein the porous membrane comprises one or more test zones, each test zone comprising one or more reagents configured to bind for detection one or more analyte of interest;

(b) a generally rigid base which supports the test strip, the base comprising a first vertical wall and a second vertical wall forming a recess which receives the base layer therewithin at the distal end of the base layer, the width of the recess being approximately equal to the width dimension of the base layer, the first vertical wall comprising one or more first structures formed thereon above the level of the base layer, and the second vertical wall comprising one or more second structures formed thereon above the level of the base layer, wherein the first and second structures are configured to retain the test strip within the base, and wherein the second bibulous material is optionally engaged by the first compression structures and the second compression structures.

The term "undercut" as used herein refers to a portion of a part's geometry that would prevent the part from being ejected from a straight-pull mold without a portion of the mold damaging the part. The simplest example of an undercut feature on a part would be a through-hole aligned perpendicular to the direction of part ejection. In certain embodiments, the undercut feature of the present invention is provided by one or more structures formed on an internal wall of the base; in these embodiments, the undercut is the space lying beneath these structures.

For purposes of the present invention, these features which establish the undercut will be referred to as "undercut structures." Such structures may be in the form of ribs, bars, spherical caps, frustums, etc. Preferably the features are radiused in profile to assist in assembly of the test device and removal of the device from the mold. In certain embodiments the undercut structures on opposing walls may be offset from one another to further aid in insertion of the test strip. In certain embodiments, once the base layer of the test strip is seated beneath the undercut structures and into the undercut, the undercut structures engage the bibulous material disposed on the base layer. This engagement can be compressive, as the bibulous material is often a compressible material, or frictional, or a combination of these forces. This engagement can assist in accurately positioning the test strip within the housing base.

As noted above, the test strip is preferably formed as a lamination of one or more bibulous materials on a substantially uncompressible and nonabsorbent base layer. The term "substantially uncompressible" as used herein refers to a material that substantially maintains its original thickness when subjected to compressive forces experienced during the insertion of the material into the undercut portion as described herein. In preferred embodiments, the base layer is also substantially nonabsorbent. The term "substantially nonabsorbent" as used herein refers to a material which is not sufficiently hydrophilic and porous as to support lateral flow of an aqueous sample.

The term "bibulous" as used herein refers to a material which is sufficiently hydrophilic and porous to support lateral flow of an aqueous sample. Such materials include cellulose papers, nitrocellulose membranes, polyvinylidine fluoride, charge modified nylon, polyethersulfone, porous polyethylene sheets, glass fiber mats, etc. This list is not meant to be limiting.

The term "test zone" as used herein refers to a discrete location on a lateral flow test strip which is interrogated in order to generate a signal related to the presence or amount of an analyte of interest. Such interrogation may be performed visually as in an over-the-counter pregnancy test, or in an instrumented fashion as through the detection of reflectance, absorption, fluorescence, luminescence, etc. by a suitably configured meter.

The term "generally rigid" as used herein in reference to the housing refers to a material which is sufficiently rigid to maintain the test strip in position relative to the other features of the device and signal detection system during use of the test device in a lateral flow assay method.

The presence and shape of internal features may influence and define the flow path through the lateral flow material. By way of example, liquid can move across the top or bottom of the lateral flow material and pool on the surface thereof. Such flow may reduce the flow through the detection region of the device, thereby reducing sensitivity. Additionally, because such aberrant flow is unpredictable, failure to control such flow contributes substantially to assay imprecision as measured by a coefficient of variation (CV). Preferably, the test devices of the present invention exhibit a CV of less than 10%.

In certain embodiments, the base and test strip form the entire test device. In certain other embodiments, a second mold assembly may be used to form a test device lid comprising a sample receiving aperture and a test aperture which can be mated to the base and enclose regions of the test strip which are not accessed (either fluidly or optically) during a test. By way of example only, a test device may be formed by introducing a moldable material into the second mold assembly to form the test device lid; removing the test device lid from the second mold assembly; and mating the test device lid to the test device base such that the sample receiving aperture overlies the first bibulous material and the test aperture overlies the one or more test zones. While the lid and base may be formed with discrete molds, the first mold assembly and the second mold assembly may be configured as a single assembly, wherein the test device base and the test device lid are formed as a unitary part. To facilitate fit of the lid and base, the test device base and the test device lid may be formed as a unitary part connected by one or more flexible hinge regions (e.g. living hinges) configured to allow the test device lid to mate to the test device base.

The foregoing description of the test devices is not intended to preclude the provision of additional zones, apertures, features, etc. commonly used in such lateral flow devices. By way of example, a conjugate pad comprising a detectable label for use in the assay can be included. When sample flows into the conjugate pad, the detector reagent solubilizes, lifts off the pad material, and moves with the sample front into the membrane. In the case of a sample such as whole blood which contains cells and other particulates, a filter matrix can be provided to The presence and shape of internal features may influence and define the flow path through the lateral flow material. By way of example, liquid can move across the top or bottom of the lateral flow material and pool on the surface thereof. Such flow may reduce the flow through the detection region of the device, thereby reducing sensitivity. In certain embodiments, the mold assembly may be configured to form a raised platform portion of the test device base. This platform is preferably configured to underlie the base layer of the test strip between the proximal and distal ends thereof and to support the test strip without contacting the porous membrane. Such a platform can be used to position the test strip away from the sidewalls and floor of the test device base to prevent capillary flow of aqueous sample along the edges of the test strip.

To further manage this unproductive flow, the mold assembly may be configured to form one or more features to retain (e.g., ribs, bumps, pins, or bars) in the test device lid and/or base, where these features are configured to engage the surface of the bibulous material and promote desired flow through the bibulous material and impede undesired flow. In certain embodiments, these retaining features contact, but do not substantially compress the bibulous material, as overcompression can reduce flow rate through the device. In particularly preferred embodiments, the retaining features may be configured to account for swelling of the lateral flow structures due to absorption of the liquid components during a test such that these retaining features contact, but do not substantially compress the bibulous material during performance of a test with the test device.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1A:
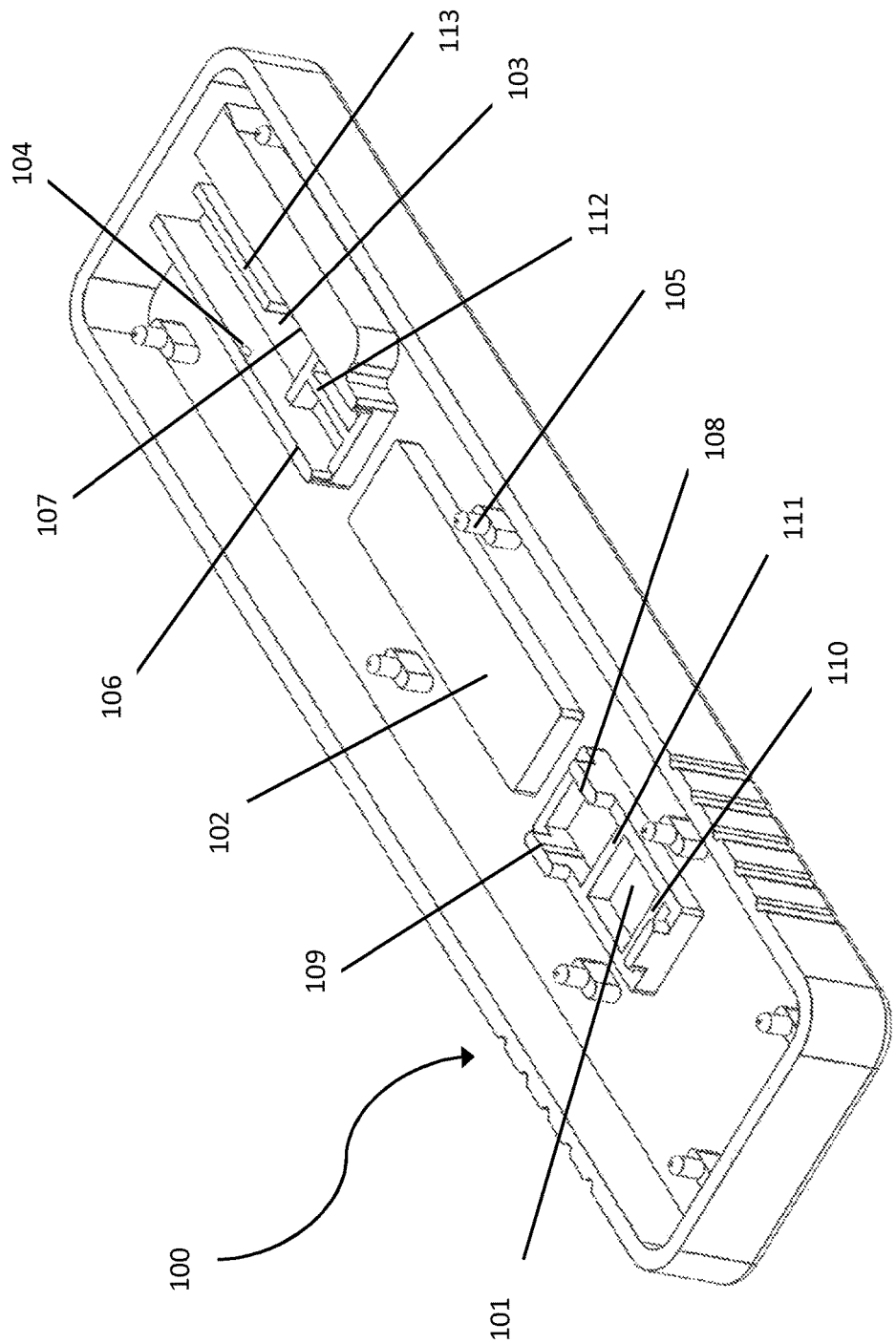
FIG. 1A depicts a perspective view of a test device base of the present invention.
Figure 1B:
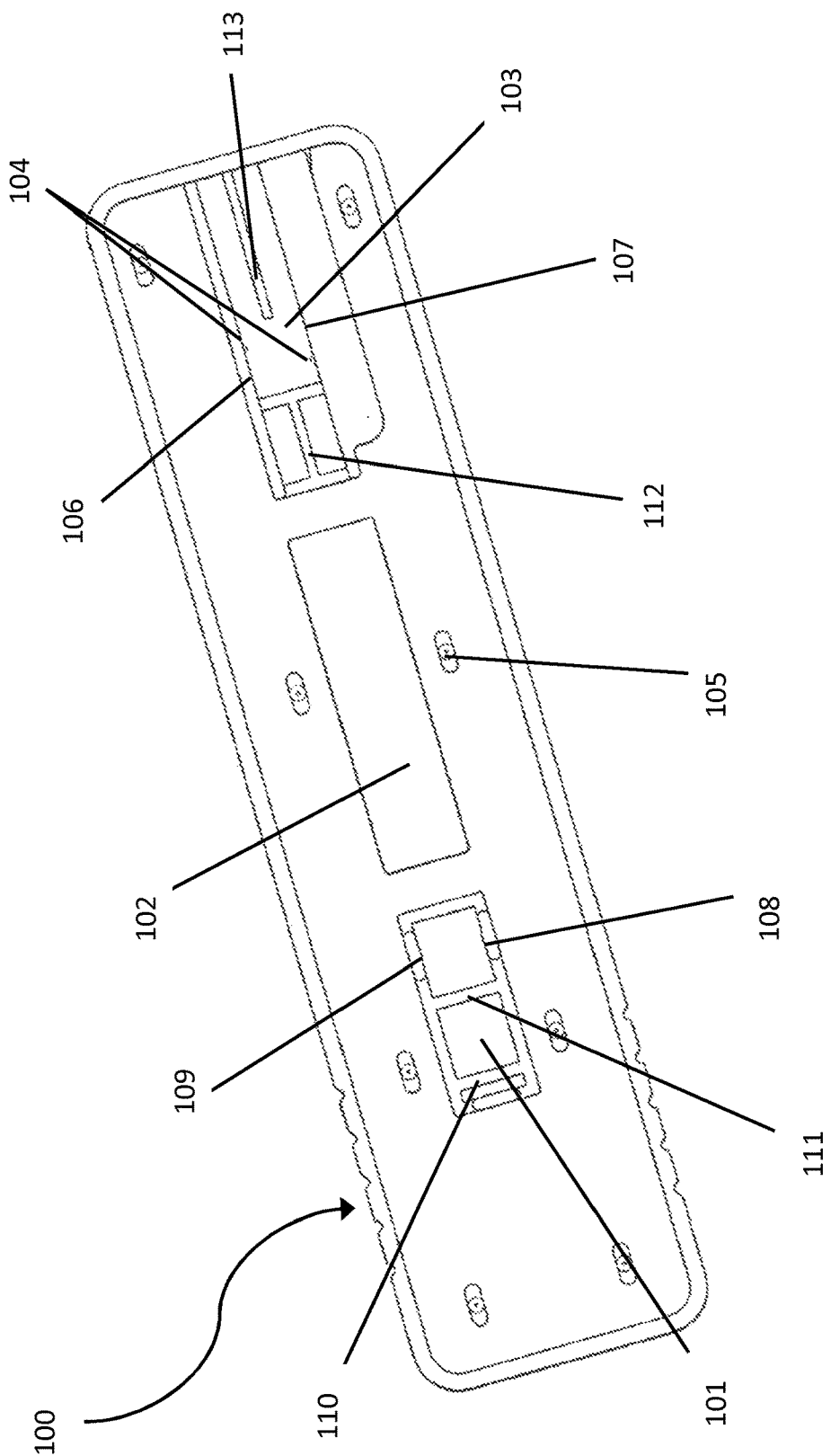
FIG. 1B depicts a top view of a test device base of the present invention.

FIGS. 1A and 1B show two views of a generally rigid base 100 configured to support a test strip. The test device base may be formed using a number of methods known to those of skill in the art, including but not limited to injection molding, blow molding, machining, etching, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold—in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

The skilled artisan will understand that a number of polymers may be used to form the test device base, including thermoplastics, some thermosets, and elastomers. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

As noted herein, the test device base of the present invention is formed to provide an undercut into which one or more components of the test strip are inserted for purposes of retaining the test strip during manufacture and use of the test device. Undercuts on molded parts are features that prevent the part from being directly ejected from the injection molding machine. Undercuts can be molded as an integral, unitary part of the test device base, but typically require a "side action," "lifter" or "collapsible core" mold component that moves separately from the two halves. In the case that the plastic material of the test device base is sufficiently flexible, a side action or other similar mold component is not always required. In these cases the undercut is stripped or snapped out of the mold. When this is done usually a stripping plate or ring is used instead of stripper pins so that the features forming the undercut are not damaged in the process of removing the part from the mold. The skilled artisan will recognize that the features forming the undercut need not be molded into the part, but may be formed by machining or etching of the part after the part is formed.

As shown in FIGS. 1A and B, the features forming the undercut are provided as small protrusions 104 in vertical walls 106 and 107. These "undercut structures." may be in the form of ribs, spherical caps, frustums, etc. Preferably the features are radiused in profile to assist in releasing the nominal geometry from the mold, and in assembly of the test device, as the radiused profile can allow the test strip to more easily slide past these structures when it is inserted from the top into recess 103. In certain embodiments, this radiused profile is only on the top surface of the structures, while the bottom surface is somewhat flat. In this way, once the test strip is inserted, it can "snap" into the undercut and fit against the flat bottom surface of the structures. In certain embodiments the undercut structures on opposing walls may be offset from one another longitudinally on vertical walls 106 and 107 as depicted in FIG. 1B to further aid in insertion of the test strip.

Figure 2:
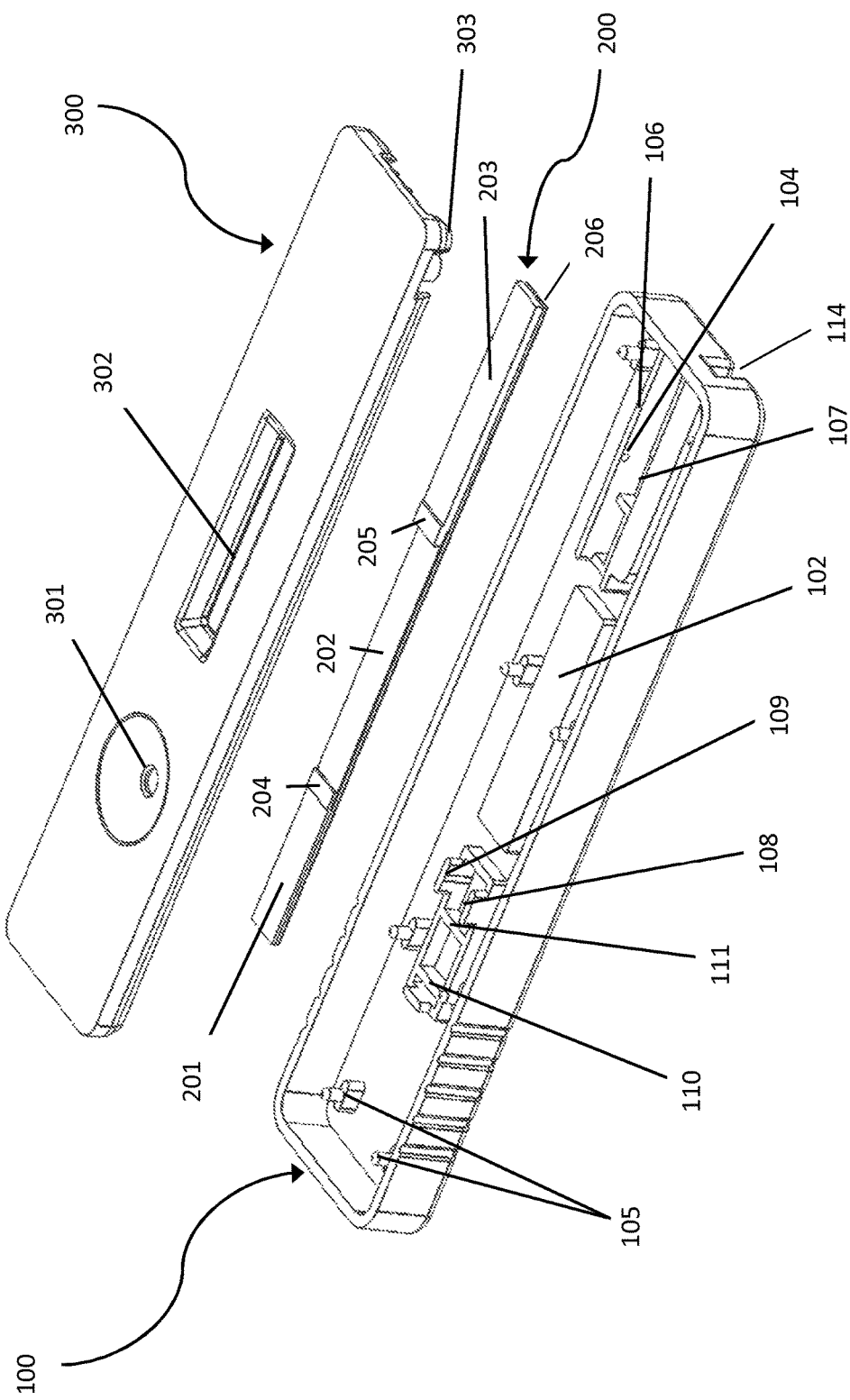
FIG. 2 depicts an exploded view of a test device of the present invention, showing the test device base, test strip, and test device lid.

FIG. 2 depicts the relative orientations of the various components of the test device. In this embodiment, a test strip 200 is mated to the test device base 100. When inserted, the proximal end 201 of the test strip lies within in recess 101 on bars 110 and 111 and between side walls 108 and 109; the central portion 202 of the test strip lies across raised platform 102; and the distal end 203 of the test strip lies within recess 103 on bars 112 and 113 and between side walls 106 and 107. The terms "proximal" and "distal" are not used in any functional sense, but rather simply to distinguish the two ends of the test strip.

The test strip 200 is configured to perform a lateral flow assay to detect the presence or amount of one or more analytes. Lateral flow assay strips typically comprise series of materials which provide capillary flow spaces. Suitable materials include materials derived from cellulose (e.g. papers), nitrocellulose, cellulose acetate, glass fibers, nylon, dacron, PVC, polyacrylamide, cross-linked dextran, agarose, polyacrylate, ceramic materials, sintered polymers, etc. The material or materials of the test strip may optionally be treated to modify their capillary flow characteristics or the characteristics of the applied sample. For example, the sample application region of the test strip may be treated with buffers to correct the pH or alter the contact angle to correct the hydrophilic character of the materials. Each of these elements has the capacity to transport fluid. The first bibulous material (sometimes referred to as the sample pad) receives the sample fluid. The fluid migrates to the second element (e.g., a nitrocellulose membrane strip) in which a chemical partner (e.g., antibody) that has been immobilized on the particle's surface participates in a binding event related to the presence or amount of an analyte of interest in the sample. The immobilized materials are provided in areas (often called stripes, reaction zones, or detection zones) which are interrogated for a detectable signal indicative of the binding event(s) of interest. After passing these zones, the fluid enters a final porous material (often referred to as a wick or waste zone) that promotes flow of sufficient sample past the detection zones. Lateral Flow Tests typically operate as either competitive or sandwich assay format, and a single device can simultaneously detect multiple analytes.

In FIG. 2, test strip 200 is formed as a laminated structure having a substantially uncompressible base layer 206, a first bibulous material disposed on the base layer at the proximal end 201 which provides a sample receiving region which promotes flow of sample to a lateral flow membrane in central portion 202. The first bibulous material and the lateral flow membrane contain a region of overlap 204 to aid in transfer of a sample from the first bibulous material to the lateral flow membrane. At the distal end 203, a second bibulous material provides the wick for the test strip. Again, the second bibulous material and the lateral flow membrane contain a region of overlap 205 to aid in transfer of a sample from the lateral flow membrane to the second bibulous material.

The substantially uncompressible base layer 206 preferably comprises a hydrophobic material so as to reduce the tendency of sample to flow along the interface between the various flow promoting materials and the base layer. Suitable materials include films made of such hydrophobic polymers such as polypropylene, polystyrene, polymethylmethacrylate, etc. The thickness of this layer is selected to provide a desired level of stiffness so as to support the lateral flow materials, and is preferably between 0.001 and 0.02 inches.

Optionally, the test device comprises a lid (or cover) 300 which serves to aid in handling of the device without contamination of the test strip. As depicted in FIG. 2, a series of posts 105 in the test device base 100 mate with corresponding posts 303 in the cover 300 to hold the cover in place in the completed test device. A sample aperture 301 provides fluid ingress to the first bibulous material, and a reading aperture or window 302 provides access to interrogate the detection zones on the porous lateral flow membrane.

In assembling the test strip 200 into the test device base 100, at least the base layer 206 is inserted into the undercut formed by undercut structures 113. Because base layer 206 has some residual flexibility, it can be inserted past the undercut structures 113 by pressing in from the top. As noted above, a radiused upper surface and staggered placement of undercut structures 113 can assist in allowing the base layer 206 to slip into the undercut. Alternatively, the test strip can be inserted into recess 103 from the end closest to platform 102 and slid into the undercut.

In certain embodiments, the second bibulous material is engaged by the undercut structures 113 when the base layer 206 is in place. This can provide compressive and/or frictional forces which assist in proper positioning of test strip 200 in test device base 100. This engagement can be on the sides of the second bibulous material, or on the upper surface of the second bibulous material.

As discussed above, lateral flow assays may be configured using a variety of detectable labels known in the art. The most commonly used label materials in visual read tests are colloidal gold particles. Other possible label modalities include enzyme, conjugates, other colloidal metals, fluorescent particles, and magnetic particles. Many label modalities (e.g., optical labels, magnetic labels, etc.) can be interrogated by instruments. Slot 114 depicts a channel which may be configured to mate with a corresponding structure within an instrument. Such elements can serve to both accurately position the test device within the instrument, and to permit only appropriate test devices to be inserted and read by the instrument.

Figure 3:
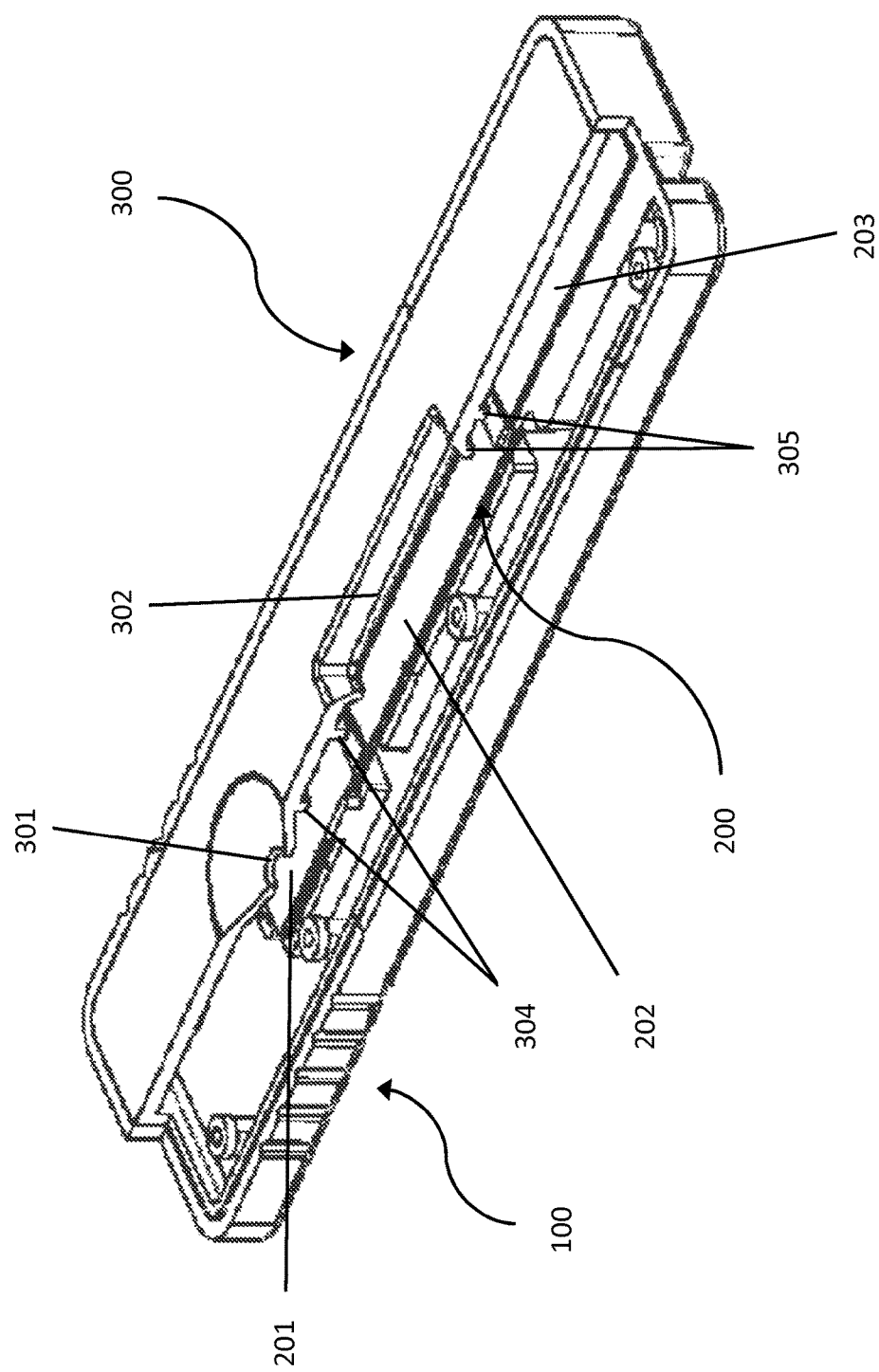
FIG. 3 depicts a cutaway view of an assembled test device of the present invention.

FIG. 3 shows the fully assembled test device, with a partial cutaway of the cover to show the relative positioning of various internal structures. Sample aperture 301 is positioned over, but not in contact with, the sample receiving region of the test strip 200. Sample flow is initiated by introduction of sample fluid into aperture 301, and subsequently occurs through the first bibulous material, aided by ribs 304 which contact the surface of the test strip and act to inhibit flow across the surface, as well as to aid in accurate position of the test strip within the device. Flow is lateral in a proximal-to-distal direction. Reading aperture 302 is positioned over, but not in contact with, the test zones of the nitrocellulose membrane. Ribs or other structures such as posts, bumps, bars, etc. 305 contact the surface of the test strip at the junction between the membrane and the second bibulous material and act to inhibit flow across the surface, as well as to aid in accurate position of the test strip within the device.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of forming a lateral flow test device, comprising:
   providing a first mold assembly which forms a test device base as a non-strippable article, the test device base comprising on a floor thereof a first vertical wall and a second vertical wall forming a recess having a defined width therebetween, the first vertical wall comprising one or more first compression structures and the second vertical wall comprising one or more second compression structures, wherein the first and second compression structures define an undercut portion between the first vertical wall and second vertical wall;
   introducing a moldable material into the first mold assembly to form the test device base;
   removing the test device base from the first mold assembly;
   providing a test strip comprising
      a substantially uncompressible and nonabsorbent base layer,
      a first bibulous material disposed on the base layer at a proximal end thereof and forming a sample receiving region,
      a second bibulous material disposed on the base layer at a distal end thereof and forming an absorbent region, wherein the second bibulous material is compressible, and
      a porous membrane disposed on the base layer between the proximal and distal ends thereof and fluidly connected to the first bibulous material and the second bibulous material,
      the test strip defining a flow path wherein a sample applied to the sample receiving region flows through the porous membrane to the absorbent region, wherein the porous membrane comprises one or more test zones, each test zone comprising one or more reagents configured to bind for detection one or more analyte of interest; and
   inserting the test strip into the test device base such that the base layer inserts into the undercut portion and such that upon completing the insertion the second bibulous material is contacted by the first compression structures and the second compression structures.

2. A method according to claim 1, further comprising providing a second mold assembly which forms a test device lid comprising a sample receiving aperture and a test aperture;
   introducing a moldable material into the second mold assembly to form the test device lid;
   removing the test device lid from the second mold assembly; and mating the test device lid to the test device base such that the sample receiving aperture overlies the first bibulous material and the test aperture overlies the one or more test zones.

3. A method according to claim 2, wherein the first mold assembly and the second mold assembly are configured as a single assembly, wherein the test device base and the test device lid are formed as a unitary part.

4. A method according to claim 3, wherein the test device base and the test device lid are formed as a unitary part connected by a hinge configured to allow the test device lid to mate to the test device base.

5. The method according to claim 2, wherein the first mold assembly further forms a raised platform portion of the test device base configured to underlie the base layer between the proximal and distal ends thereof and to support the test strip without contacting the porous membrane.

6. The method according to claim 2, wherein the second mold assembly further forms one or more first ribs and one or more second ribs in the in the test device lid, the first ribs configured to engage the upper surface of the first bibulous material, and the second ribs configured to engage the upper surface of the second bibulous material.

7. The method according to claim 2, wherein the first compression structures are offset from the second compression structures.

8. The method according to claim 2, wherein the first compression structures and the second compression structures are rounded in profile.

9. The method according to claim 8, wherein the first compression structures and the second compression structures are in the form of a spherical cap.

* * * * *

UNITED STATES PATENT AND TRADEMARK OFFICE
CERTIFICATE OF CORRECTION

PATENT NO. : 10,408,828 B2
APPLICATION NO. : 14/770451
DATED : September 10, 2019
INVENTOR(S) : Joseph Anderberg and John Van Bosch Page 1 of 1

It is certified that error appears in the above-identified patent and that said Letters Patent is hereby corrected as shown below:

In the Claims

Column 10, Claim 1, Line 53, delete the text "more reagents configured to bind for detection one or" and insert --more reagents configured to bind for detection of one or--

Column 11, Claim 6, Line 20, delete the text "or more second ribs in the in the test device lid, the first ribs" and insert --or more second ribs in the test device lid, the first ribs--

Signed and Sealed this
Thirty-first Day of December, 2019

Andrei Iancu
*Director of the United States Patent and Trademark Office*